US011844862B2

(12) United States Patent
Little et al.

(10) Patent No.: US 11,844,862 B2
(45) Date of Patent: Dec. 19, 2023

(54) TREATMENT OF OCULAR CONDITIONS UTILIZING A HISTONE/PROTEIN DEACETYLASE INHIBITOR

(71) Applicant: University of Pittsburgh—Of the Commonwealth System of Higher Education, Pittsburgh, PA (US)

(72) Inventors: Steven R. Little, Allison Park, PA (US); Michelle L. Ratay, Carnegie, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/571,197

(22) Filed: Jan. 7, 2022

(65) Prior Publication Data
US 2022/0125729 A1   Apr. 28, 2022

Related U.S. Application Data

(62) Division of application No. 16/760,295, filed as application No. PCT/US2018/058184 on Oct. 30, 2018, now Pat. No. 11,253,480.

(60) Provisional application No. 62/578,927, filed on Oct. 30, 2017.

(51) Int. Cl.
*A61K 9/16* (2006.01)
*A61P 27/02* (2006.01)
*A61K 9/00* (2006.01)
*A61K 31/167* (2006.01)

(52) U.S. Cl.
CPC .......... *A61K 9/1647* (2013.01); *A61K 31/167* (2013.01); *A61P 27/02* (2018.01); *A61K 9/0048* (2013.01)

(58) Field of Classification Search
None
See application file for complete search history.

(56) References Cited

U.S. PATENT DOCUMENTS

| | | | |
|---|---|---|---|
| 5,837,226 A | 11/1998 | Jungherr et al. | |
| 6,656,460 B2 | 12/2003 | Benita et al. | |
| 7,060,299 B2 | 6/2006 | Alavattam et al. | |
| 8,298,569 B2 | 10/2012 | Philips et al. | |
| 8,492,334 B2 | 7/2013 | Lavik et al. | |
| 9,018,006 B2 | 4/2015 | Stepkowski et al. | |
| 9,056,045 B2 | 6/2015 | Hughes et al. | |
| 11,559,428 B2 * | 1/2023 | Andino | A61M 5/31 |
| 2004/0225004 A1 * | 11/2004 | Zeligs | A61K 33/26 514/564 |
| 2006/0246145 A1 | 11/2006 | Chang et al. | |
| 2010/0048608 A1 * | 2/2010 | Klimko | A61K 31/18 514/357 |
| 2012/0148676 A1 | 6/2012 | Little | |
| 2013/0316010 A1 | 11/2013 | Lavik | |
| 2014/0271657 A1 | 9/2014 | Orkin et al. | |
| 2017/0367981 A1 | 12/2017 | Little et al. | |
| 2020/0054562 A1 * | 2/2020 | Sirianni | A61P 35/00 |

FOREIGN PATENT DOCUMENTS

WO   WO 2011/017448   2/2011

OTHER PUBLICATIONS

Ikuta et al. (Creation of Nano eye-drops and effective drug delivery to the interior of the eye, Scientific Reports, Mar. 14, 2017) (Year: 2017).*
Akimova et al., "Histone/protein deacetylases and T-cell immune responses," *Blood*, 119(11): Mar. 15, 2012.
Balaram et al., "Efficacy and tolerability outcomes after punctal occlusion with silicone plugs in dry eye syndrome," *American Journal of Opthalmology*, 131(1): 30-37, Jan. 2001.
Baudouin et al., "Role of hypersmolarity in the pathogenesis and management of dry eye disease: proceedings of the OCEAN group meeting," *The Ocular Surface*, 11(4): 246-257, Oct. 2013.
Chang et al., "Biodegradable PLGA-based drug delivery systems for modulating ocular surface disease under experimental murine dry eye," *J Clin Exp Ophthalmol*, 2(11): Nov. 1, 2011.
Guzman et al., "Desiccating stress-induced disruption of ocular surface immune tolerance drives dry eye disease," *Clinical and Experimental Immunology*, 184(2): 248-256, Dec. 21, 2015.
Ikuta et al., "Creation of nano eye-drops and effective drug delivery to the interior of the eye," *Scientific Reports*, 10 pages, Mar. 14, 2017.
International Search Report and Written Opinion issued for International Application No. PCT/US2018/058184 dated Jan. 21, 2019.
Johnson et al., "Effects of histone deacetylase inhibitor SAHA on effector and FOXP3+ regulatory T cells in rhesus macaques," *Transplantation Proceedings*, 40(2): 459-461, Mar. 2008.
Kersey et al., "Corticosteroid-induced glaucoma: a review of the literature," *Eye*, vol. 20, pp. 407-416, May 6, 2005.
Lemp et al., "Advances in understanding and managing dry eye disease," *American Journal of Ophthalmology*, 146(3): 350-356, Sep. 2008.
Liu et al., "Effect of HDACi givinostat in treating experimental ocular autoimmunity," *ARVO Meeting Abstract*, vol. 56, p. 882, Jun. 2015.
Lucas et al., "Induction of Foxp3+ regulatory T cells with histone deacetylase inhibitors," *Cellular Immunology*, 257(1-2): 97-104, Apr. 8, 2009.
Perry et al., "Evaluation of topical cyclosporine for the treatment of dry eye disease," *Arch Ophthalmol*, 126(8): 1046-1050, Aug. 11, 2008.
Quinn et al., "The Effect of HDACi givinostat on the expression of immune markers related to human ocular inflammation," *ARVO Meeting Abstract*, vol. 56, p. 883, Jun. 2015.
Tai et al., "The clinical efficacy of silicone punctal plug therapy," *Cornea*, 21(2): 135-139, Mar. 2002.

(Continued)

*Primary Examiner* — Melissa S Mercier
(74) *Attorney, Agent, or Firm* — Klarquist Sparkman, LLP

(57) ABSTRACT

A method for treating an ocular disorder in a subject comprising administering a therapeutic agent-loaded carrier to an ocular site of the subject in need thereof, wherein the therapeutic agent is a histone deactylase inhibitor.

18 Claims, 7 Drawing Sheets

(56) References Cited

OTHER PUBLICATIONS

Tao et al., "Deacetylase inhibition promotes the generation and function of regulatory T cells," *Nature Medicine*, 13(11): 1299-1307, Oct. 7, 2007.
Wang et al., "Nanoparticle formulations of histone deacetylase inhibitors for effective chemo radiotherapy in solid tumor," *Biomaterials*, vol. 51, pp. 208-215, Feb. 19, 2015.

* cited by examiner

TREATMENT OF OCULAR CONDITIONS UTILIZING A HISTONE/PROTEIN DEACETYLASE INHIBITOR

CROSS-REFERENCE TO RELATED APPLICATIONS

This is a divisional of U.S. application Ser. No. 16/760,295, filed on Apr. 29, 2020, which is the U.S. National Stage of International Application No. PCT/US2018/058184, filed Oct. 30, 2018, which was published in English under PCT Article 21(2), which application in turn claims the benefit of U.S. Provisional Application No. 62/578,927, filed Oct. 30, 2017, which is incorporated herein by reference in its entirety.

BACKGROUND

The treatments for dry eye disease are based upon the condition. Mild treatments can include lifestyle changes, such as wearing sunglasses and less exposure to drying winds. Additional therapies to aid mild to moderate inflammation are tear substitutes. Artificial tears do provide temporary relief for patients; however, most formulations contain preservatives such as benzalkonium chloride that can cause eye irritation and hyperosmolarity of the tear film. Also, anti-inflammatory treatments are used for patients with severe inflammation. These treatments have shown to decrease inflammation in patients, however are only intended for short-term use, and long-term application has been implicated in conditions such as glaucoma and retinopathy. Other treatment approaches include, tear duct plugs, which reduce tear turnover. However, plugs do not address the underlying cause of the inflammatory disease.

Dry eye disease (DED) is a multifactorial ocular condition, characterized by inflammation of the ocular surface and tear film instability, which afflicts as many as 1 in 5 individuals globally. Individuals with DED suffer symptoms including blurred vision, foreign-body and/or burning sensation, light sensitivity, and in severe cases, corneal ulcerations leading to vision loss. Current treatments predominantly address the symptoms of DED and include artificial tears, punctual occlusion with tear plugs, and ophthalmic corticosteroids. Artificial tear substitutes may provide temporary relief for patients; however, most artificial tear formulations contain preservatives, such as benzalkonium chloride, which sometimes can cause tear film hyperosmolarity. This adverse effect can trigger death of mucin-producing goblet cells, leading to further ocular irritation. Tear plugs may be used with or without artificial tears to reduce tear turnover by occluding the draining tear duct; however, these punctal plugs must be inserted by a physician, and limitations include issues with plug retention and increased risk of ocular infections. Even with regular use of artificial tears and/or punctual plugs, many patients remain symptomatic because these palliative treatments do not address the underlying cause of DED. Recently, a number of studies demonstrated an inflammatory basis for DED, which led to the application of topical corticosteroids to treat DED. While ophthalmic corticosteroids broadly suppress ocular inflammation and can alleviate symptoms of DED, the effects are transient and are prescribed for short-term use. Consequently, treatment of DED typically requires long-term use of corticosteroids, which is associated with severe side effects, such as steroid-induced glaucoma and retinopathy. Furthermore, despite suppressing production of inflammatory mediators, corticosteroids do not address the underlying imbalance between pro-inflammatory immune cells and immunosuppressive cells.

Iu DED, infiltration of pathogenic pro-inflammatory $CD4^+$ T cells causes a breakdown in immunological homeostasis, ultimately compromising the lacrimal functional unit (LFU), which includes the cornea, conjunctiva, lacrimal glands, meibomian glands, and the interconnecting innervation. As T cells proliferate in the ocular tissues, these cells secrete pro-inflammatory cytokines, such as IFN-γ, which inhibit naturally suppressive immune cells known as regulatory T cells (Tregs). This ultimately leads to a shift in the immunological balance between tissue-protective Tregs and tissue-destructive pro-inflammatory (effector) T cells. Since the importance of Tregs contributing to immunological tolerance has become evident over the years, investigators have examined methods to utilize these immunosuppressive cells. Notably, adoptive transfer of Tregs from mice with DED can suppress inflammation in a T-cell deficient nude mouse administered effector T-cells from a DED mouse. Moreover, due to the low population of Tregs found in the human body (5-15%), application of ex vivo transfer of Tregs has been proposed as a method of therapeutic modulation in order to enhance the limited numbers of Tregs. Despite such evidence suggesting that enhancing Treg populations ex vivo is a viable therapeutic approach, there are many hurdles associated with translating a cellular therapy to the clinic. These include expansion, contamination, and the potential hazard of Tregs differentiating into conventional T cells.

SUMMARY

Disclosed herein is a method for treating an ocular disorder in a subject comprising administering a therapeutic agent-loaded carrier to an ocular site of the subject in need thereof, wherein the therapeutic agent is a histone deactylase inhibitor.

Also disclosed herein is a method for treating Sjögren's syndrome in a subject comprising administering a therapeutic agent-loaded carrier to an ocular site of the subject in need thereof, wherein the therapeutic agent is a histone deactylase inhibitor.

Additionally disclosed herein is a composition comprising therapeutic agent-loaded microparticles, wherein the therapeutic agent is a histone deactylase inhibitor.

The foregoing will become more apparent from the following detailed description, which proceeds with reference to the accompanying figures.

DETAILED DESCRIPTION

Terminology

Figure 1:
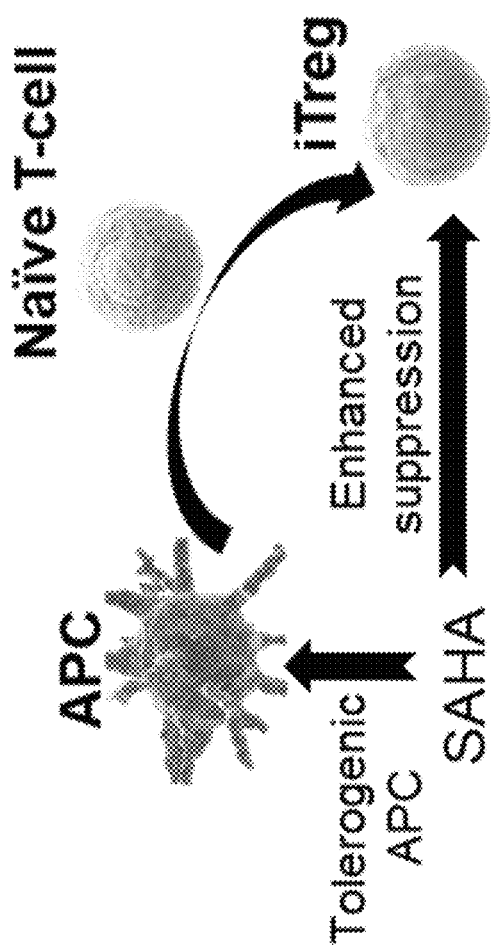
FIG. 1 is a schematic representation of mechanisms of action for suberoylanilide hydroxamic acid (SAHA).

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats.

The term "co-administration" or "co-administering" refers to administration of an agent disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks. In certain embodiments, a plurality of therapeutic and/or diagnostic agents may be co-administered by encapsulating the agents within the microparticles disclosed herein.

"Inhibiting" refers to inhibiting the full development of a disease or condition. "Inhibiting" also refers to any quantitative or qualitative reduction in biological activity or binding, relative to a control.

"Microparticle", as used herein, unless otherwise specified, generally refers to a particle of a relatively small size, but not necessarily in the micron size range; the term is used in reference to particles of sizes that can be, for example, administered to the eye in the form of an eye drop that can be delivered from a squeeze nozzle container, and thus can be less than 50 nm to 100 microns or greater. In certain embodiments, microparticles specifically refers to particles having a diameter from about 200 nm to 30 microns, or about 1 to about 25 microns, preferably from about 10 to about 25 microns, more preferably from about 10 to about 20 microns. In one embodiment, the particles have a diameter from about 1 to about 10 microns, preferably from about 1 to about 5 microns, more preferably from about 2 to about 5 microns. As used herein, the microparticle encompasses microspheres, microcapsules, microparticles, microrods, nanorods, nanoparticles, or nanospheres unless specified otherwise. A microparticle may be of composite construction and is not necessarily a pure substance; it may be spherical or any other shape.

"Ocular region" or "ocular site" means any area of the eye, including the anterior and posterior segment of the eye, and which generally includes, but is not limited to, any functional (e.g., for vision) or structural tissues found in the eyeball, or tissues or cellular layers that partly or completely line the interior or exterior of the eyeball. Ocular regions include the anterior chamber, the posterior chamber, the vitreous cavity, the choroid, the suprachoroidal space, the subretinal space, the conjunctiva, the subconjunctival space, the episcleral space, the intracorneal space, the epicorneal space, the sclera, the pars plana, surgically-induced avascular regions, the macula, the retina, and the lacrimal functional unit (LFU), which includes the cornea, conjunctiva, lacrimal glands, meibomian glands, and the interconnecting innervation.

"Ocular condition" means a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition. For example, a "therapeutically effective amount" may be a level or amount of agent needed to treat an ocular condition, or reduce or prevent ocular injury or damage without causing significant negative or adverse side effects to the eye or a region of the eye "Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as dry eye disease. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments, "treating" means reduction or resolution or prevention of an ocular condition, ocular injury or damage, or to promote healing of injured or damaged ocular tissue "Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, PA (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The development of formulations that can induce endogenous Tregs in vivo using a single small molecule therapeutic agent would drastically diminish concerns of clinical safety and regulations. One particular potential category of drugs that could serve to simplify clinical translation is a class of small molecules known as histone deacetylase inhibitors (HDACi). Specifically, this class of small molecules are known to induce differentiation and cell cycle arrest in cancer cells. An HDACi known as suberoylanilide hydroxamic acid (SAHA) (N-hydroxy-N'-phenyl-octanediamide; vorinostate) has been approved by the FDA for cutaneous T cell lymphoma (Commercially referred to as Zolinza®; Merck & Co., Inc., Whitehouse Station, NJ). In addition, to its usage as an anti-cancer therapeutic, this small molecule drug has been attracting interest as a potential anti-inflammatory therapeutic. Moreover, HDACi have recently shown to enrich/enhance the local populations of effector T cells and Tregs. Specifically, the HDACi, SAHA, promotes Foxp3 acetylation, thereby increasing the binding of Foxp3 to DNA and enhancing suppressive functions of natural Tregs (nTregs) as shown in FIG. 1. Also, SAHA can also induce the generation of tolerogenic APCs via acetylation and activation of STAT-3, which can then lead to differentiation of induced Tregs (iTregs) as shown below in FIG. 1.

Given that a HDACi can both expand Tregs and enhance their immunosuppressive function, we believe that a HDACi will effectively cause the local induction of Tregs and prevent clinical symptoms associated with DED. Accordingly, disclosed herein are compositions that can sustainably release a HDACi in order to modulate Treg responses locally for DED. Specifically, a local controlled delivery system was utilized to promote the peripheral conversion of naïve CD4+ T cells into iTregs. The compositions can encapsulate and locally release a HDACi, and thus may be able to prevent damage to the ocular tissue, enhance mRNA FoxP3 expression, and reduce the pro-inflammatory microenvironment observed in DED.

The controlled release formulations disclosed herein are highly effective at reducing the proinflammatory milieu in the ocular tissue, which is essential to the maintenance of immunological homeostasis to ensure the prevention of chronic inflammation. Overall, the current topical therapeutics focus on acting as antagonists (ex: Xiidra) to hinder a specific cell involved in the pathogenesis of inflammatory eye diseases. While on the other hand, the use of these microparticles is an approach to restore the homeostatic balance instead of solely targeting a pathogenic cell. Therefore, this treatment will resolve the underlying etiology of the disease and provide a long-term ophthalmic drug delivery system. The methods and compositions disclosed herein also could result in a dramatic increase of patient compliance and reduce disease morbidity.

In particular, disclosed herein are methods and compositions for treating ocular disorders. In certain embodiments, the ocular disorder is a non-infectious ocular disease. Illustrative disorders include, but are not limited to, dry eye disease, uveitis, allergic conjunctivitis, scleritis and Age-Related Macular Degeneration (AMD). In certain embodiments, the disorder is an inflammatory mediated ocular disorder, particularly in cases with chronic inflammation as an underlying cause.

By ameliorating inflammation in the lacrimal glands, the therapeutic agent-loaded carrier approach disclosed herein also could be used to be used to treat Sjögren's syndrome, an autoimmune disease targeting the lacrimal and salivary glands that causes a severe form of DED and dry mouth.

The methods include administering a therapeutic agent-loaded carrier to a subject, wherein the therapeutic agent includes a histone deactylase inhibitor (HDACi). The carrier may be in the form of a thin film, a rod, contact lens, or microparticles. In certain embodiments, the compositions include therapeutic agent-loaded microparticles.

Illustrative therapeutic agents include a subset of inhibitors that are a small molecule pan-HDACi (act on all isoforms of the zinc-dependent enzymes) that may cause epigenetic modifications that regulate gene expression and protein function in order to modulate the function of immune cells such as T lymphocytes. In particular, HDACi can stimulate thymic production of anti-inflammatory Tregs, enhance Treg suppressive function, and promote the peripheral conversion of CD4+ naïve T cells into Tregs.

Illustrative histone deactylase inhibitors include suberoylanilide hydroxamic acid (SAHA) (N-hydroxy-N'-phenyl-octanediamide); trichostatin A(TsA); entinostat (MS-275); panobinostat (LBH589); mocetinostat (MGCD); romidepsin (FK228, Depsipeptide); belinostat (PXD101); MC1568; givinostat (ITF2357); quisinostat (JNJ-26481585) 2HCl; droxinostat; AR-42; tacedinaline (CI994); valproic acid sodium salt (Sodium valproate); tacedinaline (CI994), Sodium butyrate; resminostat; divalproex sodium; sodium phenylbutyrate; tubastatin A; scriptaid; TMP269; BRD73954; LMK-235; (−)-parthenolide; nexturastat A; CAY10603; 4SC-202; BG45; and ITSA-1 (ITSA1). In certain embodiments, the histone deactylase inhibitor is suberoylanilide hydroxamic acid (SAHA) (N-hydroxy-N'-phenyl-octanediamide).

In certain embodiments, the therapeutic agents are highly effective at inducing and/or enhancing the immunosuppressive function of Tregs, which is essential to the maintenance of immunological homeostasis to ensure the prevention of chronic inflammation and autoimmunity.

In one embodiment, disclosed herein are therapeutically-relevant, modular platforms to deliver therapeutic agents in vivo by artificial particles into the vicinity of Tregs. In one embodiment, the delivered agents modulate Treg cell proliferation. In one embodiment, the delivered factors modulate Treg cell immunosuppressive capacity.

In one embodiment, the method comprises introducing artificial microparticles in vivo wherein Tregs are recruited and/or activated. In one embodiment, the Treg cell recruitment and/or activation induces biological homeostasis thus resolving the ocular disease or condition.

In certain embodiments, the amount of agent loaded into the microparticles may range from 1 ng to 1 mg, more particularly 1 to 100 µg, and most particularly, 20 to 30 µg agent per mg of microparticles. In certain specific embodiments, the amount of agent loaded into the microparticles is 25-30 µg agent per mg of microparticles.

The polymers for the microparticle may be bioerodible polymers so long as they are biocompatible. Preferred bio-erodible polymers are polyhydroxyacids such as polylactic acid and copolymers thereof. Illustrative polymers include poly glycolide, poly lactic acid (PLA), and poly (lactic-co-glycolic acid) (PLGA). Another class of approved biodegradable polymers is the polyhydroxyalkanoates.

Other suitable polymers include, but are not limited to: polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly (methyl acrylate), poly(isopropyl acrylate), poly(isobutyl acrylate), poly(octadecyl acrylate), polyethylene, polypropylene polyethylene glycol), poly(ethylene oxide), poly(ethylene terephthalate), poly(vinyl alcohols), poly(vinyl acetate), poly vinyl chloride polystyrene, polyvinylpryrrolidone, alginate, poly(caprolactone), dextran and chitosan.

The percent loading of an agent may be increased by "matching" the hydrophilicity or hydrophobicity of the polymer to the agent to be encapsulated. In some cases, such as PLGA, this can be achieved by selecting the monomer ratios so that the copolymer is more hydrophilic for hydrophilic drugs or less hydrophilic for hydrophobic drugs. Alternatively, the polymer can be made more hydrophilic, for example, by introducing carboxyl groups onto the polymer. A combination of a hydrophilic drug and a hydrophobic drug can be encapsulated in microparticles prepared from a blend of a more hydrophilic PLGA and a hydrophobic polymer, such as PLA.

A preferred polymer is a PLGA copolymer or a blend of PLGA and PLA. The molecular weight of PLGA is from about 10 kD to about 80 kD, more preferably from about 10 kD to about 35 kD. The molecular weight range of PLA is from about 20 to about 30 kDa. The ratio of lactide to glycolide is from about 75:25 to about 50:50. In one embodiment, the ratio is 50:50.

Illustrative polymers include, but are not limited to, poly(D,L-lactic-co-glycolic acid) (PLGA, 50:50 lactic acid to glycolic acid ratio, $M_n$=10 kDa, acid-terminated, referred to as 502H); poly(D,L-lactic-co-glycolic acid) (PLGA, 50:50 lactic acid to glycolic acid ratio, $M_n$=25 kDa, acid-terminated, referred to as 503H); poly(D,L-lactic-co-glycolic acid) (PLGA, 50:50 lactic acid to glycolic acid ratio, $M_n$=30 kDa, acid-terminated, referred to as 504H); poly(D, L-lactic-co-glycolic acid) (PLGA, 50:50 lactic acid to glycolic acid ratio, $M_n$=35 kDa, ester-terminated, referred to as 504); and poly(D,L-lactic-co-glycolic acid) (PLGA, 75:25 lactic acid to glycolic acid ratio, $M_n$=10 kDa, referred to as 752).

In certain embodiments, the polymer is an ester-terminated PLGA.

In certain embodiments, the polymer is a polyethylene glycol-poly(lactic-co-glycolic acid) copolymer.

In certain embodiments, the polymer microparticles are biodegradable.

In certain embodiments, the agent-loaded microparticles may have a volume average diameter of 200 nm to 30 μm, more particularly 1 to 30 μm. In certain embodiments, the agent-loaded microparticles do not have a volume average diameter of 10 μm or greater since such larger particles are difficult to eject from a container in the form of an eye drop. The agent-loaded microparticles may be pore less or they may contain varying amounts of pores of varying sizes, typically controlled by adding NaCl during the synthesis process.

In certain embodiments, the agent-loaded microparticle-containing composition does not include a hydrogel, particularly a thermoresponsive hydrogel.

The agent-loaded microparticle fabrication method can be single or double emulsion depending on the desired encapsulated agent solubility in water, molecular weight of polymer chains used to make the microparticles (MW can range from ~1000 Da to over 100,000 Da) which controls the degradation rate of the microparticles and subsequent drug release kinetics.

The microparticle disclosed herein may provide for sustained release of an agent. For example, the sustained release may be over a period of at least one day, more particularly at least 5 days or at least 10 days, and most particularly at least 30 days. The agent release can be linear or non-linear (single or multiple burst release). In certain embodiments, the agent may be released without a burst effect. For example, the sustained release may exhibit a substantially linear rate of release of the therapeutic agent in vivo over a period of at least one day, more particularly at least 5 days or at least 10 days, and most particularly at least 30 days. By substantially linear rate of release it is meant that the therapeutic agent is released at a rate that does not vary by more than about 20% over the desired period of time, more usually by not more than about 10%. It may be desirable to provide a relatively constant rate of release of the agent from the delivery system over the life of the system. For example, it may be desirable for the agent to be released in amounts from 0.1 to 100 μg per day, more particularly 1 to 10 μg per day, for the life of the system. However, the release rate may change to either increase or decrease depending on the formulation of the polymer microparticle. In certain embodiments, the delivery system may release an amount of the therapeutic agent that is effective in providing a concentration of the therapeutic agent in the eye in a range from 1 ng/ml to 200 μg/ml, more particularly 1 to 5 μg/ml. In certain embodiments, there is no initial lag phase of release. The desired release rate and target drug concentration can vary depending on the particular therapeutic agent chosen for the drug delivery system, the ocular condition being treated, and the subject's health.

The microparticle disclosed herein may provide for controlled release of an agent. The term "controlled release" as used herein, refers to the escape of any attached or encapsulated factor at a predetermined rate. For example, a controlled release of an agent may occur resulting from the predicable biodegradation of a polymer particle (i.e., for example, an artificial antigen presenting cell). The rate of biodegradation may be predetermined by altering the polymer composition and/or ratios comprising the particle. Consequently, the controlled release may be short term or the controlled release may be long term. In one embodiment, the short term release is between 30 minutes-1 hour. In one embodiment, the short term release is between 1 hour-3 hours. In one embodiment, the short term release is between 3 hours-10 hours. In one embodiment, the short term release is between 10 hours-24 hours. In one embodiment, the long term release is between 24 hours-36 hours. In one embodiment, the long term release is between 3 days-7 days. In one embodiment, the long term release is between 7 days-1 month. In one embodiment, the long term release is between 1 month-6 months. In one embodiment, the long term release is between 6 months-1 year. In one embodiment, the long term release is at least one year.

In certain embodiments the agent-loaded microparticles may be included in a composition suitable for topical administration in the form of a liquid eye drop. The eye drop(s) may be administered to any ocular structure. The eye drops may be self-administered by the subject. The eye drop will conform comfortably to the conjunctival sac and release the loaded agent. The eye drop may be administered on a regimen wherein the interval between successive eye drops is greater than at least one day (although in certain embodiments the eye drop may be administered once daily or more than once daily). For example, there may be an interval of at least 5 days, at least one week, or at least one month between administrations of an eye drop(s). The agent-loaded microparticles disclosed herein drastically decreases the dosing frequency (thereby increasing the likelihood of patient compliance and recovery/prevention of worsening symptoms), it does so while avoiding clinician involvement for administration by being completely noninvasive.

The microparticle-containing composition disclosed herein may include an excipient component, such as effective amounts of buffering agents, and antioxidants to protect a drug (the therapeutic agent) from the effects of ionizing radiation during sterilization. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents are advantageously present in amounts sufficient to maintain a pH of the system of between about 2 to about 9 and more preferably about 4 to about 8. As such the buffering agent may be as much as about 5% by weight of the total system. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight.

In certain embodiments, the microparticles disclosed herein may be administered via injection. Injection sites include but are not limited to intraorbital lacrimal gland, extraorbital lacrimal gland, intraorbital injection, subconjunctival, intravitreal, posterior and anterior chambers of the eye.

EXAMPLES

Figure 2:
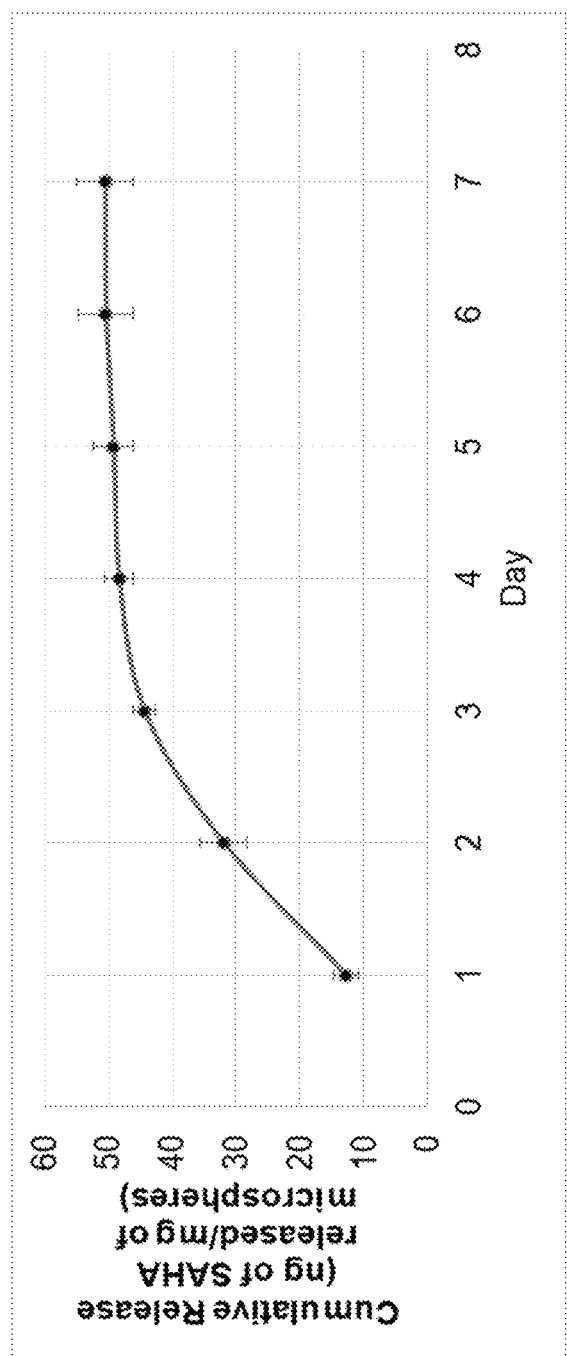
FIG. 2 is a graph showing the controlled release of SAHA.
Figure 4:
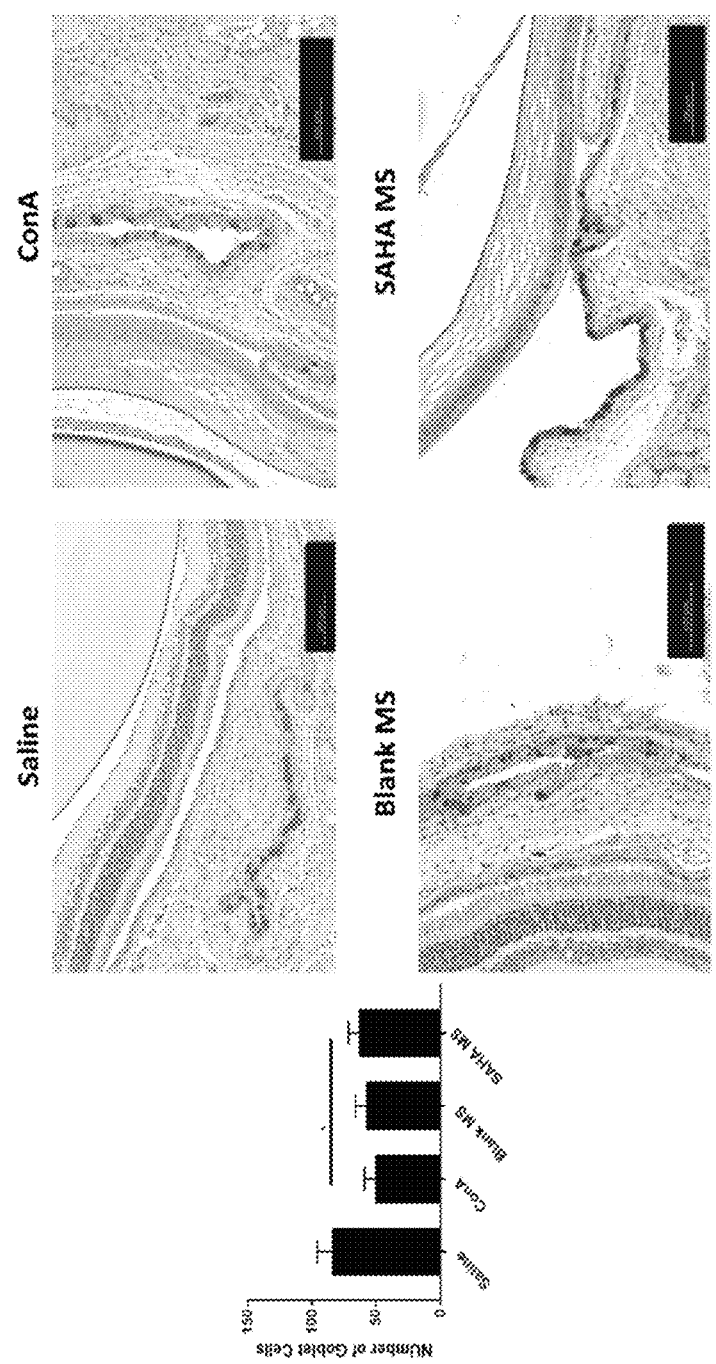
FIG. 4 is a graph showing goblet cell density and histological sections of the conjunctiva.
Figure 5:
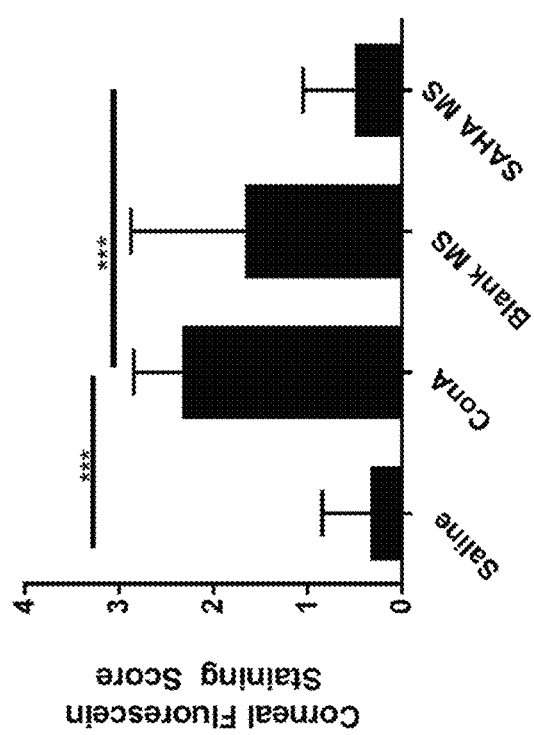
FIG. 5 shows fluorescein staining of the corneal epithelium.
Figure 5:
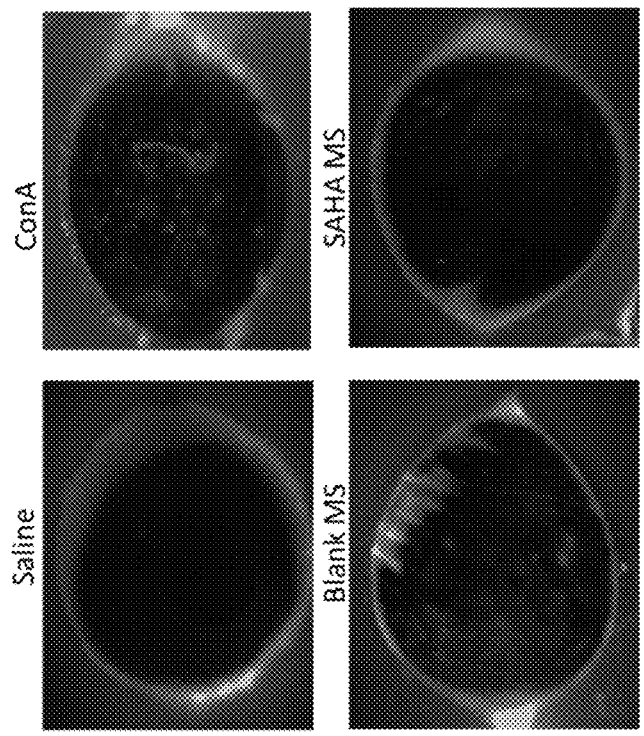

A controlled release formulation encapsulating SAHA was fabricated to provide sustained local delivery to the ocular tissue. The formulation was developed using PLGA and engineered to release SAHA over the course of one-week shown in FIG. 2. Notably, the data suggest that the local administration of the SAHA MS in the ocular tissue was able to prevent clinical signs of DED. A common clinical sign of DED is a reduction of overall tear production, which subsequently can lead to ocular dryness and irritation. While aqueous tear secretion in ConA (diseased) and ConA+Blank MS treated control mice was significantly reduced, as expected, SAHA MS treatment prevented ConA-induced loss of aqueous tear secretion shown in FIG. 3. In addition to preserving aqueous tear production, effective therapeutics should also maintain the composition of tears by protecting gel-forming, mucin-producing goblet cells. These goblet cells are located on the apical surface of the conjunctiva and produce important/key non-aqueous components of the tears. Interestingly, loss of goblet cells in ocular tissue in DED is reportedly due to an increase in the pro-inflammatory milieu. Thus, in this study, histological sections of the conjunctiva were examined to determine whether SAHA MS preserved mucin-producing goblet cells after the administration of SAHA MS. Indeed, we observed significantly greater goblet cell density in SAHA MS-treated mice, compared to diseased (ConA) mice, as shown in FIG. 4. Since loss of aqueous tear production and/or mucin-producing goblet cells in DED ultimately leads to damage to the ocular surface, we investigated whether SAHA MS, which prevented both of these pathological features, also maintained integrity of the corneal epithelium. Corneal integrity was assessed with fluorescein, a dye that stains dead epithelial cells and can diffuse into areas where cellular tight junctions are compromised. Punctate staining was observed in mice with DED induced by ConA (with or without Blank MS), as shown in FIG. 5. Notably, there was a 4-fold reduction in the average fluorescein staining score in the SAHA MS group as compared to the ConA alone, suggesting that the HDACi was able to prevent the damage to the ocular tissue initiated by ConA.

Figure 6:
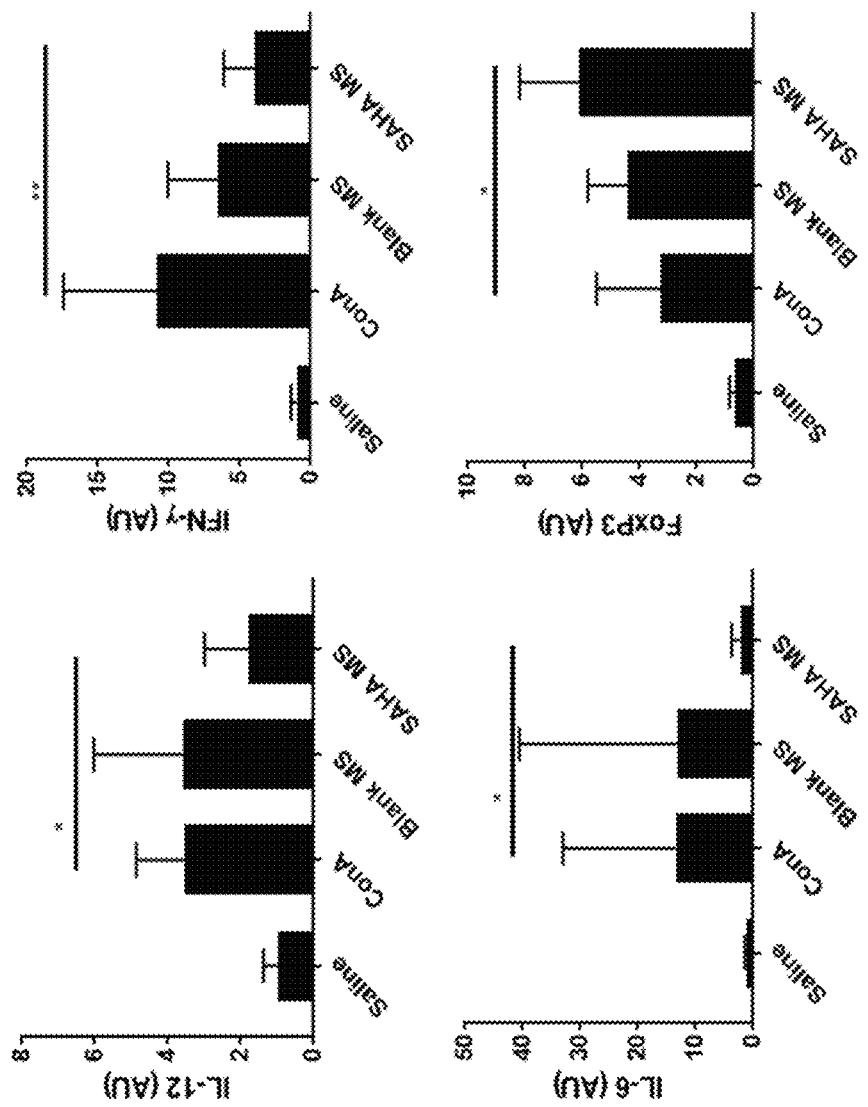
FIG. 6 are graphs showing IL-12, IFN-γ, IL-6, and $FoxP3^+$ Tregs levels.

The underlying pathogenesis of DED involves effector T cells that infiltrate the ocular tissue and secrete pro-inflammatory cytokines, which can directly affect the health of the ocular microenvironment. Since increases in pro-inflammatory cytokines have been found in the lacrimal gland tissues of mice with DED, we investigated whether the SAHA MS-mediated prevention of clinical signs of DED was due to a reduced pro-inflammatory milieu in the ocular tissue. Specifically, mRNA expression levels of pro-inflammatory cytokines (IL-12, IFN-γ, and IL-6) in the lacrimal gland tissue was evaluated by qRT-PCR. Expression of IL-12 was induced by ConA injection, relative to saline controls, which may be attributed to ConA acting as a T-cell mitogen thus enhancing the expression of certain genes involved in T-cell activation such as IL-12. As expression of IL-12 is known to enhance the secretion of IFN-γ by Th1 cells, we also observed a significant increase in IFN-γ mRNA levels in the ConA group as shown in FIG. 6. Both of these findings in the ConA-induced murine model of DED are consistent with previous reports indicating that IL-12 and IFN-γ are upregulated in tears of patients with DED. In addition to increases in IL-12 and IFN-γ in the lacrimal gland, IL-6 was also significantly elevated in the ConA treatment group, which is consistent with other reports of increased IL-6 production in lacrimal glands of DED murine models. Importantly, treatment with SAHA MS significantly inhibited the ConA-induced expression of IL-12, IFN-γ, and IL-6 shown in FIG. 6. These reductions in the expression levels of pro-inflammatory cytokines sparked the question of whether the SAHA MS were potentially altering the immunological microenvironment by increasing anti-inflammatory Tregs. Previous reports have demonstrated that HDACi can expand FoxP3$^+$ Tregs in vitro and in vivo. Interestingly, there was a significant rise in FoxP3 expression of Tregs locally in the lacrimal gland tissue, potentially suggesting that the reduction of signs of DED and pro-inflammatory microenvironment in the lacrimal gland may be due to Tregs suppressing the ocular inflammation shown in FIG. 6.

In summary, administration of SAHA MS preserved aqueous tear production and mucin-producing goblet cells and prevented damage to ocular tissue by reducing the pro-inflammatory milieu in the lacrimal gland and enhancing numbers and/or function of FoxP3$^+$ Tregs in an inflammatory murine model of DED.

Materials and Methods

Fabrication of HDACi Microspheres

HDACi microspheres were fabricated using a single-emulsion evaporation technique due to the hydrophobic nature of SAHA. Specifically, 200 mg of Poly (lactic-co-glycolic) acid (PLGA-50:50 lactide:glycolide, acid terminated) (MW:7,000-17,000) (viscosity: 0.16-0.24 dL/g, 0.1% (w/v) (Sigma Aldrich, MO) was used to encapsulate 40 mg of SAHA (Selleck Chem, TX) in 4 ml of dichloromethane and sonicated for 1 hour. Subsequently, this emulsion was then mixed with 60 ml of 2% polyvinyl-alcohol (PVA, MW ~25,000, 98% hydrolyzed; PolySciences) and homogenized (L4RT-A, Silverson, procured through Fisher Scientific) at 3,500 rpm for 1 min. Then the homogenized mixtures were added to 80 ml of 1% PVA on a stir plate and left for approximately 1.5 hours in order for the organic solvent to evaporate. After 1.5 hours, the microspheres were centrifuged (200 g, 5 min, 4° C.), washed 4 times with deionized water, and lyophilized for 48 hours (Virtis Benchtop K freeze dryer, Gardiner, NY).

Characterization of HDACi Microspheres

The morphology of the microspheres was characterized using scanning electron microscopy (SEM) (JEOL, JSM-6330F, Peabody, MA) and volume impedance measurements were performed on a Beckman Coulter Counter (Multisizer- 3, Beckman Coulter, Fullerton, CA). In order to determine the release kinetics of the SAHA microspheres, 10 mg of the fabricated microspheres with drug (SAHA) or unloaded microspheres (composed of no drug only polymer-as a control) were added to 1 ml of 0.2% Tween 80 in PBS (Sigma Aldrich, St. Louis, MO), which was placed onto a rotator at 37° C. The supernant was sampled daily and the release profile was determined using a NanoDrop 2000 Spectrophotometer (ThermoFisher Scientific, MA).

Mice

Female Balb/c mice aged 6-8 weeks were utilized for this experimental study. (Charles Rivers Laboratories, Wilmington, MA). All murine experiments were approved by the Institutional Animal Care and Use Committee, University of Pittsburgh, Pittsburgh, Pa.

Murine Model 10 mg/ml of Concanavalin A (ConA) (Sigma Aldrich, St. Louis, MO) in phosphate buffered saline solution (PBS) was injected into the lacrimal glands with a dissecting microscope (Olympus SZX10, Waltham, MA) in order to induce an inflammatory-murine model of DED. (10 mg/ml of either Blank MS or SAHA MS were administered together with ConA).

Tear Production

In order to measure tear production, phenol red cotton threads were utilized. (Oasis Medical, San Dimas, CA). Specifically, the phenol red thread was placed in the lateral canthus of the eye for a period of 60 seconds, and the amount of tears absorbed onto the thread (when tears are absorbed onto the thread a color change occurs from yellow to red) was measured using a dissecting microscope (Olympus SZX10, Waltham, MA).

Corneal Fluorescein Staining

Approximately 1 μl of fluorescein (1% solution in PBS) was applied to the conjunctival sac. Subsequently, the ocular surface was examined using a dissecting microscope (Olympus SZX10, Waltham, MA) to identify punctate staining. The scoring of staining was completed by a masked ophthalmologist, and scored 0 for no staining, score 1 for a quarter of staining, score of 2 for less than a half, score of 3 for half, and 4 for more than half of the eye.

Ocular Histology

At the end of the one-week study, murine eyes were exenterated and fixed in 10% neutral buffered formalin solution for a period of 48 hours. Then paraffin embedded sections were cut at approximately 5 μm and stained with Periodic Acid Schiff (PAS). These histological sections were scanned and the goblet cell density was quantified using a Zeiss Axio Scan. Z1 (Thornwood, NY) and Panoramic Viewer software (3D HISTECH Ltd.).

qRT-PCR

Total RNA was extracted from excised lacrimal glands using TRI-reagent (Molecular Research Center, Cincinnati, OH), and quantified using a NanoDrop 2000 (Thermo Scientific). For the reverse transcriptase assay, 2 μg RNA was converted to cDNA using a QuantiTect Reverse Transcription Kit (Qiagen, Valencia, CA). Quantitative real-time PCR was then performed using VeriQuest Probe qPCR Mastermix (Affymetrix, Santa Clara, CA), (Thermo Scientific) specific for (IFN-γ:Mm01168134_m1, FAM-MGB dye), (IL-12: Mm01288989_m1, FAM-MGB dye), (IL-6: Mm00446190_m1, FAM-MGB dye),(FoxP3: Mm00475162_m1, FAM-MGB dye) and (Gusb: Mm01197698_m1, VIC-MGB PL dye, endogenous control). Duplex reactions (target gene+GUSB) were run and analyzed on a StepOnePlus Real-Time PCR System (Applied Biosystems, Carlsbad, CA). Relative fold changes of IFN-γ, IL-12, IL-6, and FoxP3 expression were calculated and normalized based upon the $2^{-\Delta\Delta Ct}$ method, with the Saline group as the untreated control.

Statistical Analysis

Data expressed as mean±S.D. Comparisons between multiple treatment groups were performed using one-way ANOVA, followed by Bonferroni multiple comparisons, and $p \leq 0.05$ was considered statistically significant. For PCR data, a Grubb's test was performed to determine any significant outliers. If a significant outlier was found (P>0.05) it was excluded from the statistical analysis. If an assumption of the One-Way ANOVA was not met a non-parametric test was performed. Statistical tests were performed using GraphPad Prism Software 6.0 (GraphPad Prism, San Diego, CA).

Results

Characterization of SAHA Microspheres

Figure 7:
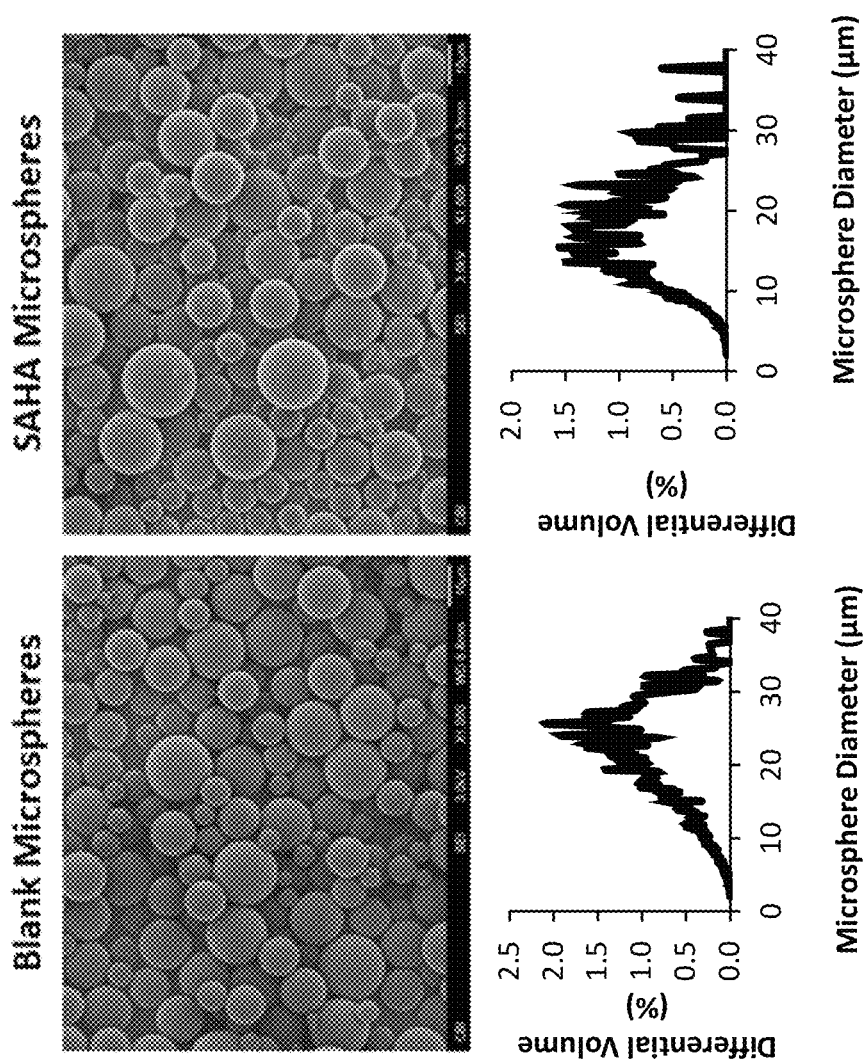
FIG. 7 are scanning electron micrographs showing the morphology of microparticles and graphs showing the average size distribution of microparticles.

SAHA MS were fabricated using the polymer (PLGA 50:50-lactic:glycolic acid, RG 502H). Scanning electron micrographs (SEM) as shown in FIG. 7 illustrate that individual particles are spherical with average size distribution average of ~16.956 μm (Blank Microspheres) and an average of ~17.099 μm (SAHA Microspheres) as confirmed by utilizing a Coulter Counter (representative plots of volume impedance measurements shown below in FIG. 7. Additionally, the release kinetics was characterized using a NanoDrop (UV-vis spectrophotometer) to detect the absorbance of SAHA, which demonstrates a cumulative release of approximately 50 ng/mg of microsphere.

Aqueous Tear Production is Maintained with SAHA Microspheres

Figure 3:
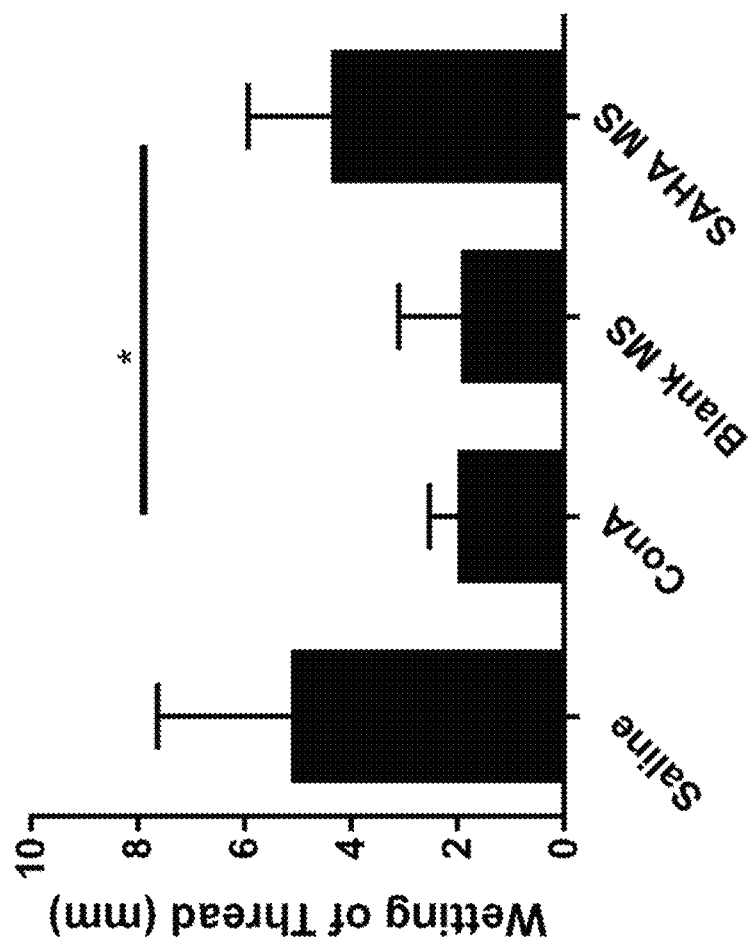
FIG. 3 is a graph showing tear secretion.

To determine whether SAHA MS were capable of preventing key signs of DED, aqueous tear secretion was examined using phenol red threads at the conclusion of the experimental study.[7] The administration of Saline (non-diseased) did not significantly affect tear production compared to ConA alone (diseased) and ConA+Blank MS as shown in FIG. 3. Markedly, the loss of tear production was prevented with the administration of SAHA MS.

SAHA Microspheres Decrease Corneal Fluorescein Staining

A hallmark of DED is an increase of permeability to the corneal epithelial layer of the ocular tissue. Specifically, fluorescein staining is a standard diagnostic measurement/indicator for disease severity of ocular surface damage.[9] Representative corneal fluorescein images were captured using a fluorescent dissecting microscope and scored by a masked ophthalmologist on a scale of 0 to 4, with 0 corresponding to no staining, and 4 corresponding to staining on more than 50% of the cornea, as seen in FIG. 5. Compared to the ConA alone and ConA+Blank MS group, the uptake of fluorescein to the cornea was significantly reduced in the Saline and SAHA MS groups. Ultimately, the local administration of SAHA MS to lacrimal gland demonstrated (*** $p \leq 0.001$) that the preventative therapy was able to reduce the corneal fluorescein scores by approximately % 0% compared to the ConA alone group.

The Administration of SAHA Microspheres Prevent Loss of Goblet Cell Density

Goblet cells are located within the stratified columnar conjunctival epithelial cells, and are known to play an integral role in producing, mucin, a component of the tears. Moreover, goblet cells have been associated with the production of MUC5AC, which acts as a gel layer to trap pollen and allergens. As these goblet cells are depleted due to chronic inflammation due to conditions such as DED this can ultimately lead to conjunctival epithelial squamous metaplasia and an abnormal tear film. Thus, Periodic Acid Schiff (PAS staining) of the ocular tissue was examined to determine whether SAHA MS were able to reduce the loss of goblet cells compared to ConA alone thereby potentially preserving the goblet cells (pink/purple cells) located in the conjunctiva. Notably, there was a significant preservation of goblet cell density with the administration of SAHA MS as compared to the ConA alone group.

mRNA Expression Altered in the Lacrimal Gland with SAHA Microspheres

As inflammation occurs to the lacrimal gland, this has shown to lead to an infiltration of lymphocytes and subsequently an increase in pro-inflammatory cytokines. Thus, mRNA expression levels were examined in the lacrimal gland tissue after ConA-induced inflammation. Data from the RT-PCR suggested that IL-12, IFN-γ, and IL-6 pro-inflammatory cytokines were significantly reduced in the lacrimal gland of the SAHA MS treated as compared to the ConA (diseased) group. Although, interestingly, the level of FoxP3 (transcription factor of regulatory T cell marker) mRNA expression was significantly higher in the SAHA MS group as compared to the ConA (diseased) group, as seen in FIG. 6. Together, this data indicates that the SAHA MS was able to reduce the pro-inflammatory microenvironment initiated by ConA and enhance the expression levels of FoxP3 (a transcription factor associated with Tregs).

In view of the many possible embodiments to which the principles of the disclosed invention may be applied, it should be recognized that the illustrated embodiments are only preferred examples of the invention and should not be taken as limiting the scope of the invention.

What is claimed is:

1. A method for treating an ocular disorder in a subject comprising administering a therapeutic agent-loaded carrier to an ocular site of the subject in need thereof, wherein the therapeutic agent is a histone deactylase inhibitor, and wherein the ocular disorder is dry eye disease.

2. The method of claim 1, wherein the histone deactylase inhibitor is suberoylanilide hydroxamic acid (SAHA) (N-hydroxy-N'-phenyl-octanediamide); trichostatin A(TsA); entinostat (MS-275); panobinostat (LBH589); mocetinostat (MGCD); romidepsin (FK228, Depsipeptide); belinostat (PXD101); MC1568; givinostat (ITF2357); quisinostat (JNJ-26481585) 2HCl; droxinostat; AR-42; tacedinaline (CI994); valproic acid sodium salt (Sodium valproate); tacedinaline (CI994), Sodium butyrate; resminostat; divalproex sodium; sodium phenylbutyrate; tubastatin A; scriptaid; TMP269; BRD73954; LMK-235; (–)-parthenolide; nexturastat A; CAY10603; 4SC-202; BG45; or ITSA-1 (ITSA1).

3. The method of claim 1, wherein the histone deactylase inhibitor is suberoylanilide hydroxamic acid (SAHA).

4. The method of claim 1, wherein the therapeutic agent loaded-carrier provides controlled delivery of the therapeutic agent under conditions suitable for inducing and/or enhancing the immunosuppressive function of regulatory T cells to an ocular region of interest or inducing regulatory T cells in an ocular region of interest.

5. The method of claim 4, wherein the regulatory T cells are endogenous.

6. The method of claim 1, wherein the therapeutic agent-loaded carrier is in the form of therapeutic agent-loaded microparticles.

7. The method of claim 1, wherein the therapeutic agent-loaded carrier comprises therapeutic agent-loaded microparticles.

8. The method of claim 6, wherein the microparticles comprise poly (lactic-co-glycolic acid).

9. The method of claim 2, wherein the therapeutic agent-loaded carrier comprises therapeutic agent-loaded microparticles.

10. The method of claim 9, wherein the microparticles comprise poly (lactic-co-glycolic acid).

11. A method for treating an ocular disorder in a subject comprising administering a composition comprising therapeutic agent-loaded microparticles to an ocular site of the subject in need thereof, wherein the therapeutic agent is a histone deactylase inhibitor, the microparticles comprise poly (lactic-co-glycolic acid), and the composition is in the form of an eye drop, wherein the ocular disorder is dry eye disease, allergic conjunctivitis, or scleritis.

12. The method of claim 11, wherein the ocular disorder is dry eye disease.

13. The method of claim 11, wherein the method ameliorates inflammation in the subject's lacrimal glands.

14. The method of claim 1, wherein the therapeutic agent-loaded carrier is a controlled release agent.

15. The method of claim 11, wherein the histone deactylase inhibitor is suberoylanilide hydroxamic acid (SAHA) (N-hydroxy-N'-phenyl-octanediamide); trichostatin A(TsA); entinostat (MS-275); panobinostat (LBH589); mocetinostat (MGCD); romidepsin (FK228, Depsipeptide); belinostat (PXD101); MC1568; givinostat (ITF2357); quisinostat (JNJ-26481585) 2HCl; droxinostat; AR-42; tacedinaline (CI994); valproic acid sodium salt (Sodium valproate); tacedinaline (CI994), Sodium butyrate; resminostat; divalproex sodium; sodium phenylbutyrate; tubastatin A; scriptaid; TMP269; BRD73954; LMK-235; (–)-parthenolide; nexturastat A; CAY10603; 4SC-202; BG45; or ITSA-1 (ITSA1).

16. The method of claim 11, wherein the histone deactylase inhibitor is suberoylanilide hydroxamic acid (SAHA).

17. The method of claim 12, wherein the histone deactylase inhibitor is suberoylanilide hydroxamic acid (SAHA) (N-hydroxy-N'-phenyl-octanediamide); trichostatin A(TsA); entinostat (MS-275); panobinostat (LBH589); mocetinostat (MGCD); romidepsin (FK228, Depsipeptide); belinostat (PXD101); MC1568; givinostat (ITF2357); quisinostat (JNJ-26481585) 2HCl; droxinostat; AR-42; tacedinaline (CI994); valproic acid sodium salt (Sodium valproate); tacedinaline (CI994), Sodium butyrate; resminostat; divalproex sodium; sodium phenylbutyrate; tubastatin A; scriptaid; TMP269; BRD73954; LMK-235; (–)-parthenolide; nexturastat A; CAY10603; 4SC-202; BG45; or ITSA-1 (ITSA1).

18. The method of claim 12, wherein the histone deactylase inhibitor is suberoylanilide hydroxamic acid (SAHA).

* * * * *